(12) United States Patent
Agrawal et al.

(10) Patent No.: US 10,768,615 B2
(45) Date of Patent: Sep. 8, 2020

(54) SYSTEM AND METHOD FOR AUTOMATED HOSPITAL BEDS

(71) Applicants: Sanskar Agrawal, Pennington, NJ (US); Sanskriti Agrawal, Pennington, NJ (US)

(72) Inventors: Sanskar Agrawal, Pennington, NJ (US); Sanskriti Agrawal, Pennington, NJ (US)

(*) Notice: Subject to any disclaimer, the term of this patent is extended or adjusted under 35 U.S.C. 154(b) by 314 days.

(21) Appl. No.: 15/904,542

(22) Filed: Feb. 26, 2018

(65) Prior Publication Data
US 2019/0265691 A1    Aug. 29, 2019

(51) Int. Cl.
| | |
|---|---|
| *G05D 1/00* | (2006.01) |
| *G05D 1/02* | (2020.01) |
| *G01C 21/00* | (2006.01) |
| *G01C 21/20* | (2006.01) |
| *B66B 1/24* | (2006.01) |
| *B66B 1/34* | (2006.01) |
| *A61G 7/05* | (2006.01) |
| *A61B 5/00* | (2006.01) |
| *G16H 40/20* | (2018.01) |

(Continued)

(52) U.S. Cl.
CPC ......... *G05D 1/0027* (2013.01); *A61B 5/6892* (2013.01); *A61B 5/742* (2013.01); *A61B 5/7475* (2013.01); *A61G 7/0528* (2016.11); *B66B 1/2408* (2013.01); *B66B 1/3461* (2013.01); *G01C 21/005* (2013.01); *G01C 21/206* (2013.01); *G05D 1/0212* (2013.01); *G05D 1/0217* (2013.01); *G05D 1/0276* (2013.01); *G16H 40/20* (2018.01); *A61G 2203/16* (2013.01); *A61G 2203/18* (2013.01); *A61G 2203/20* (2013.01); *A61G 2203/40* (2013.01); *A61G 2203/44* (2013.01); *G01G 19/52* (2013.01); *G05D 1/0225* (2013.01); *G05D 2201/0206* (2013.01); *G06F 3/0488* (2013.01); *G08G 9/02* (2013.01); *G10L 15/22* (2013.01); *G10L 2015/223* (2013.01); *H02J 7/0013* (2013.01); *H02J 7/025* (2013.01)

(58) Field of Classification Search
None
See application file for complete search history.

(56) References Cited

U.S. PATENT DOCUMENTS

| | | | |
|---|---|---|---|
| 2007/0167385 A1* | 7/2007 | Monteleone ....... | C12N 15/1136 514/44 A |
| 2007/0174965 A1* | 8/2007 | Lemire ................ | A61G 7/005 5/600 |

(Continued)

*Primary Examiner* — Thomas G Black
*Assistant Examiner* — Demetra R Smith-Stewart
(74) *Attorney, Agent, or Firm* — Standley Law Group LLP; James L. Kwak

(57) ABSTRACT

The present invention is directed toward a system and method for effectively managing, transporting, and taking care of patients in a hospital facility. Primarily this is done through the use of an automated bed with corresponding controls and devices installed within the facility. Precautionary fail safes are implemented such that any medical profession can override the system should an error be detected. Constant monitoring and control of all automated beds may occur from a centralized system. These systems and methods will allow for better allocation of hospital resources, providing much more efficient care to all patients.

17 Claims, 6 Drawing Sheets

(51) Int. Cl.
    *G01G 19/52*     (2006.01)
    *G06F 3/0488*     (2013.01)
    *G10L 15/22*     (2006.01)
    *G08G 9/02*     (2006.01)
    *H02J 7/00*     (2006.01)
    *H02J 7/02*     (2016.01)

(56) References Cited

U.S. PATENT DOCUMENTS

| | | | |
|---|---|---|---|
| 2007/0272493 A1* | 11/2007 | Legez | B66B 1/20 |
| | | | 187/313 |
| 2008/0300777 A1* | 12/2008 | Fehr | G01C 21/20 |
| | | | 701/532 |
| 2014/0090171 A1* | 4/2014 | Hyde | A61G 1/0275 |
| | | | 5/600 |
| 2016/0005300 A1* | 1/2016 | Laufer | G08B 21/245 |
| | | | 340/573.1 |
| 2016/0038361 A1* | 2/2016 | Bhimavarapu | H04B 10/1149 |
| | | | 5/600 |

* cited by examiner

SYSTEM AND METHOD FOR AUTOMATED HOSPITAL BEDS

CROSS-REFERENCE TO RELATED APPLICATIONS

This application is a nonprovisional application and does not claim priority to any application.

TECHNICAL FIELD

Exemplary embodiments of the present invention relate to systems and methods for effectively managing, transporting, and taking care of patients in a hospital facility.

BACKGROUND

Hospitals remain one of the most hectic and stressful environments to work in. The importance of timing and efficient management of all resources is critical to providing the best care. Nurses are often understaffed and overworked. Nurses are responsible for a wide range of essential tasks from administering medicine at appropriate times to the transportation of patients from room to room. The current hospital bed is ill equipped to meet the ever-pressing demands placed on nurses and other health-care professions. The cumbersome and time-consuming process of manually requiring at least one, likely two or more, people to accomplish the simple task of transporting a bed from one room to another needlessly wastes valuable resources that could be utilized elsewhere in the hospital. What is needed in the art is a better system of transporting patients around a hospital or other health-care facility. The present invention seeks to address this problem.

BRIEF SUMMARY OF THE INVENTION

The present invention is directed to an automated hospital bed. The bed may use a series of sensors installed within the bed and within the hospital to facilitate movement about the facility. The bed may be battery powered with charging stations located on the wall or floor of many rooms in the hospital. The system will allow for central management control of all beds from a single control center. The automated bed system will allow for better allocation of hotel resources and personnel.

DETAILED DESCRIPTION OF THE INVENTION

Various embodiments of the invention will now be described in detail with reference to the accompanying drawing. These figures are merely provided to assist in the understanding of the invention and are not intended to limit the invention in any way. One skilled in the art will recognize that various modifications and changes may be made to any of these example embodiments without departing from the scope and spirit of the present invention.

Figure 1:
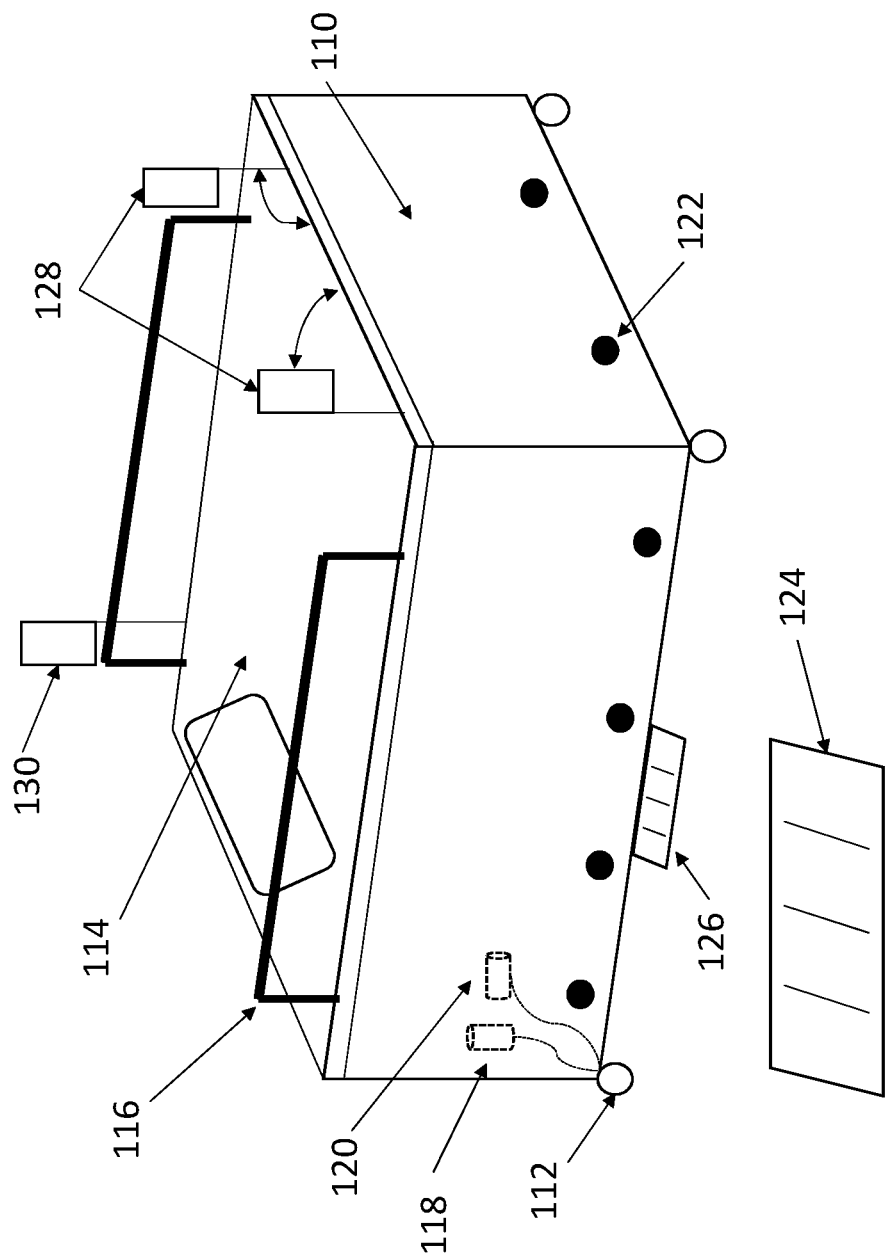
FIG. 1 depicts an exemplary embodiment of the invention.

Referring to FIG. 1, an example embodiment of the bed is depicted. The general structure will require a frame or chassis 110 connected to wheels 112 with a cushioned mattress top 114. Located at both sides of the bed along the mattress 114 may be cushioned railing 116 to prevent a patient from rolling off the bed during transportation. These rails 116 may be retractable into the chassis such that when the bed is not in motion, the rails 116 will not provide a hinderance to a patient freely getting out of the bed. For safety, these rails 116 should be activated for all bed movements with a patient.

The wheels 112 will be connected with motors 118, 120. A directional motor 118 may be responsible for turning the bed by turning the wheels 112 up to 90 degrees left or right. A drive train motor 120 may be responsible for rotating the wheels 112 forward or backward to facilitate movement of the bed. Both the directional motor 118 and drive train motor 120 may be connected in a variety of ways. For example, the directional motors 118 may be connected to the front wheels while the drive train motors 120 may be connected to the back wheels. Additionally, multiple sets of motors 118, 120 may be used to control multiple sets of wheels 112. One skilled in the art will recognize there are many ways to facilitate movement of the bed based on location of motors and the associated wheels, and any examples herein are not intended to limit the present invention in any way. The motors will control the speed of the bed. Although the speed may vary at different times for a variety of reasons, such as urgency of matter, fragility of patient, traffic conditions in hallways, etc., the bed may typically operate at about 3 miles per hour, a comfortable walking pace. Moreover, turns around corners will be precise and gradual so as to prevent the bed from getting stuck or obstructing all foot traffic during the turn.

Figure 2:
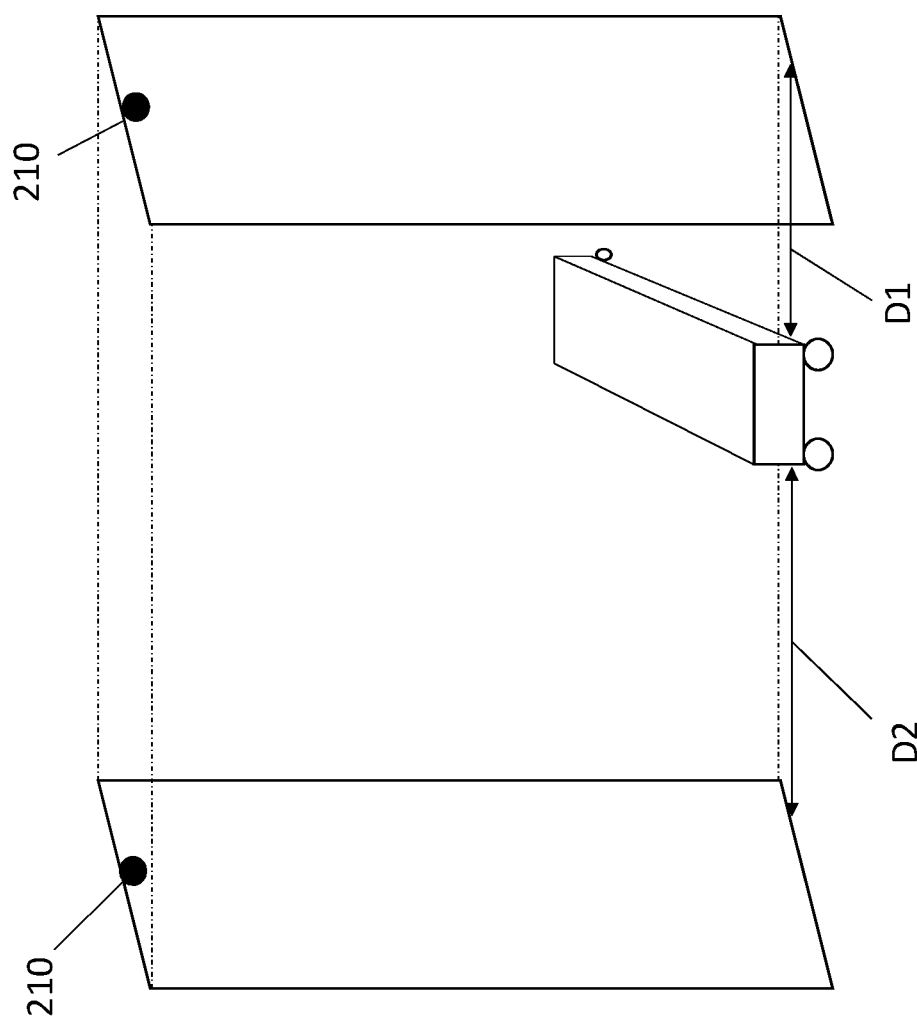
FIG. 2 depicts an embodiment within a hallway.

The bed may have a plurality of automated bed sensors (ABS) 122. The depicted embodiment has 4 ABS on a left and right side, 2 ABS on the front, and 2 ABS on the back. Although the bed may operate with a single sensor on each side, at least two are preferable. If one sensor were to fail, the device would still be operable until a repair may occur. Should multiple ABS fail on a single bed at a given time, an alert may be sent to a central management system to notify appropriate personnel to either correct the problem or switch the patient to a new bed. The ABS will be used to sense obstructions and maintain proper distances therefrom. Referring to FIG. 2, the ABS will also work in conjunction with wall sensors (WS) 210. These WS will preferably be installed in the ceiling but may operate similarly at any location on the wall. Although the system may operate with only a single WS covering a given area, preferably at least two sensors will cover the same area. In the case of failure of one of the WS, the system may operate at full performance until maintenance can correct the problem.

These WS should be located in each room and each hallway. There is no given spacing that the WS must be placed apart, but preferably, WS are spaced such that the entire floorplan of the hospital is covered. For example, if the hallway WS have a range of 10 feet, the next sensor should be placed no greater than 20 feet away to account for the entire distance between the two. Each bed may be given a unique identifying code readable by a WS such that the location of a bed at any given time is always known.

Identification codes may also be used as a means of scheduling certain bed movements tied to a patient's needs.

The size of the bed may vary, but preferably, the size is less than half of the hallway width of the hospital. Keeping the size to a minimum will allow for two lanes of traffic through the halls. Either multiple beds may be traveling in different directions down the same hallway, or a single bed may be travelling with space for human traffic to navigate freely around. If the standard size bed allowing for two lanes of traffic is insufficient for a patient due to obesity, a medical condition, or otherwise, a larger size bed may be available, and the system will take into account the need for the entire hallway in determining an acceptable route for hallway movement.

The bed will be powered by a plurality of rechargeable batteries installed within the frame 110. These batteries may be solid state, lithium ion batteries or any other suitable replacement. Multiple charging pads 124 will be available throughout the facility. These charging stations 124 may appear in each operating room, patient's room, or even a designated room for vacant beds specifically for storage and charging. The charging stations 124 may rely on the safer DC (as opposed to AC) for charging beds. The beds may have a connector 126 located on the bottom of the bed to contact the DC charging pad. This connector 126 may retract into the frame of the bed 110, for ease of movement, when not located directly above a charging pad 124. Alternatively, if a wireless form of charging is installed, such as QI technology, no retraction would be required. Charging pads 124 may be used to power stationary beds directly while simultaneously charging batteries to full capacity. Upon disconnecting from a charging pad, the battery will take over supplying power to the bed and its accessories such that no lapse in power is recognized. When a bed is not in use by a patient and has a deficient charge, the bed may automatically route itself to a designated charging room, designated patient room, or the closest, empty patient room to connect itself to a charging pad 124.

Should any of the bed equipment require AC power, the bed will be adapted to convert the DC power to AC. The DC charging pads should operate at a low enough power level such that there is little to no risk of electric shock or electrocution should a human come in contact with a pad. Furthermore, additional safeguards may be in place to prevent any such shock from occurring. There may be retractable covers installed within the floor to cover any charging pad when not in use. The WS may also be able to detect when there is no bed in a room or when the bed in the room is not located over the charging pad. The WS may communicate with the DC power supply to cut off all power transmissions to that specific charging pad until such time that a bed is detected above it. For more safety, the batteries may have an insulated, fireproof surrounding such that if a failure were to occur, the risk of the fire spreading through the bed and to the patient/hospital is minimal. Additionally, a heat sensor may be installed in close proximity to the battery. This heat sensor may be connected to a fire extinguisher. Should the heat sensor read a value above a predetermined threshold, the fire extinguisher may automatically be activated as a preventative measure. Any time a heat sensor increases beyond the threshold, a notification will be sent to the central management system, allowing for the sending of a new bed to replace the overheated one and allowing for quick action by hospital staff to ensure patient safety.

The bed may also have monitors 128 installed for the display of important patient information and additional control of bed operations beyond the central management system's control. For example, the monitors may be connected to other bed functions to display heart rate, blood pressure, temperature, and other vitals or patient information. These monitors 128 may fold inward inside the bed frame or along the end of the bed. Traditionally, any monitoring devices would also need to be dragged alongside the bed to transport a patient from one room to another, requiring multiple personnel. Having these monitors and displays attached to the bed frees up hospital resources to attend to other needs.

Figure 3:
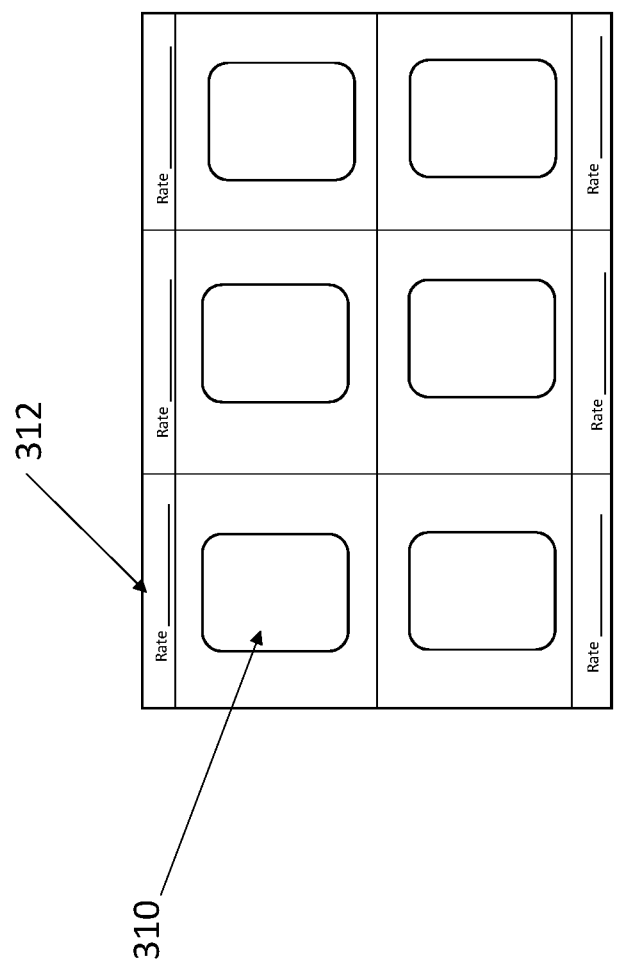
FIG. 3 depicts an exemplary IV storage compartment.

The bed may also contain a stand for IV pouches 130. These IV pouches may be stored within the bed itself, for easy access by medical professionals. When an IV pouch is nearing depletion, the system may alert the central maintenance system. The patient's timing and rate of flow for their IV bags may be displayed on the monitors 128 such that the hospital professional can accurately administer the proper dose. FIG. 3 depicts the storage of IV bags within the bed. This embodiment contains 6 IV bags 310 with the associated flow rate 312 labeled accordingly. A medical profession will have no difficulty determining which IV the patient needs at the correct time, all stored at a convenient location within the bed itself.

The bed may contain a plurality of compartments to store medical equipment, patient medicines, food, and any other materials as may be needed for proper patient care. These compartments may be locked and set to timers based on when the compartment's contents are needed. For example, for a patient capable of taking required medication every 4 hours, a single dose may be stored in a locked compartment with the patient alerted by an alarm and unlocking of the compartment at the appropriate time. Such compartments may contain weight sensors to confirm the patient did, at the very least, take the medicine out of the compartment, presumably consuming the medication as well. The compartments may also store emergency drugs, such as epinephrine, morphine, or a sedation drug, in case a patient's condition unexpectedly turns. Having the emergency medication readily available at the patient's bedside may be the difference in saving the patient's life. These emergency drugs should remain under a lock mechanism until a healthcare profession unlocks by means of a key, monitor input, spoken password, or other unlocking means.

The patient will be able to send a signal to the central maintenance system by pressing a button. This function will allow a patient to garner the attention of medical staff should he or she need anything. Additionally, the automated bed system may operate on biometrics. A patient may simply be able to ask for help and a signal will be sent to hospital staff. Biometrics may also be used for hospital staff to control the beds. Voice commands may be used to stop a bed as it is being transported, unlock a specific compartment, override the system in case of emergency, and any other functions controlled by the central management system. Certain embodiments may require each hospital staff member's voice to be stored in a database for biometric verification. Such a system may be essential when a hospital professional is within audible reach of more than one bed. Should a nurse be escorting a bed from one room to another and shout a "stop" command, the system will be able to recognize the bed assigned to that nurse and only stop the appropriate bed instead of every bed within audible range.

Although the bed may be responsive to voice commands from patients, the specific commands available to them will be limited. The patient may have limited bed movement within his or her room or to the nearest bathroom, but any attempted movement beyond the approved bounds will alert the central management system. Furthermore, certain patient commands may need to be verified by hospital personnel before the bed responds. For example, if a diabetic patient is allowed to open a compartment containing food, a medical professional may have to confirm the patient's glucose levels (this may be done remotely through constant monitoring) before permitting the compartment to open.

The automated bed may communicate via wi-fi to the main computer and database system. The central system may be responsible for directing the bed to move toward a specific destination via a specified route. When a bed move request is made, either from the patient, medical professional at the bed, or the central management system, the central system will be able to calculate the best route for the bed to take. The central system may do this by analyzing many factors such as distance to destination, current hallway traffic, urgency of the situation, etc. The central system may also continue to calculate the best route even after the bed has begun moving. Should an obstruction or emergency be detected along the current route, a new route can seamlessly be communicated to the bed. The beds will be able to automatically route themselves to designated areas at specific times without the need from central management input. If a bed is not in use and low on battery, it may reroute itself to a charging station. If the bed is in need of maintenance, it may reroute itself to a repair room. If the bed is in need of having the sheets and blankets replaced, an alert may be sent to notify a nurse. The beds will be capable of receiving movement commands from both the central management system and a nearby medical profession. Such commands may include, but not be limited to or limited by, direction of movement, speed, stop and go, and distance to travel.

The ABS and WS may be used to map the hospital environment. Any information they collect will be stored in a database and used to determine efficient use of hospital resources. Referring to FIG. 2, the ABS on the left and right side of the bed will be used to control the distance away from each side of the hallway. One side of the bed will be used to keep the bed a distance D1 away from a wall, and the other side will be used to keep the bed a distance D2 away from the opposite wall, where D1+D2+bed width is the total width of the hallway. A similar method may be used in rooms to ensure the bed is in the proper location, especially for rooms containing floor charging pads. The central management systems may create virtual lanes within hallways to better control traffic. For example, if a hallway is 10 feet wide, the hallway may be virtually designated as a two-lane hallway with each lane being 5 feet. This virtual lane may be communicated to all beds such that when routing occurs the bed will seek to stay within this 5-foot wide lane, allowing the other lane for use by pedestrians or other beds.

Figure 4:
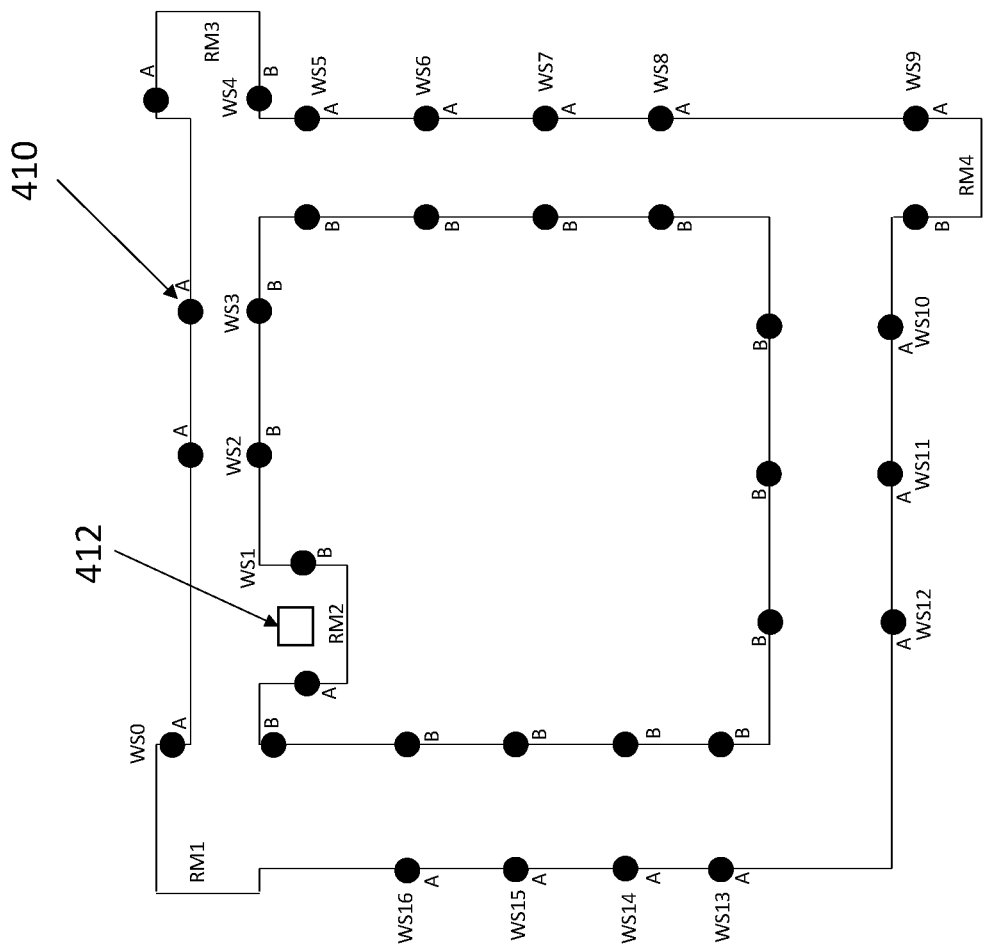
FIG. 4 depicts a hospital floor layout with wall sensors installed.

The bed may communicate with the WS ahead in the route for effective movements. Referring to FIG. 4, each WS 410 may be given a unique identifier. In the depicted figure, there are redundant sensors on the interior walls and exterior walls. An example identifier may be WS2, with WS2A representing the WS2 sensor located on an external wall and WS2B representing the WS2 sensor located on the corresponding internal wall. For a patient, and the associated bed 412, to get from their room RM2 to the operating room RM4, the following route may be taken: WS1->WS2->WS3->WS5->WS6->WS7->WS8->WS9. When an automated bed leaves the patient's room RM2, it communicates with the next sensor WS2 and moves in that direction. Instructions to move from WS1 to WS2 are stored in the database and retrieved by the movement software. Similarly, when the bed reaches WS2, it then begins to communicate with WS3. The necessary speed, distance, and time may be used to calculate the necessary motor functions to travel between adjacent WS, each of which may be stored in the database. The system will be able to calculate alternate routes and send a bed on the most efficient path. If there were an obstruction at WS3, the patient's bed may instead be routed to the operating room RM4 via WS1->WS0->WS16->WS15->WS14->WS13->WS12->WS11->WS10->WS9.

The system will also allow for automated movement between floors of the facility by controlling doors and elevators. As an automated bed approaches a WS designated for an elevator, the elevator may be called and the doors opened upon reaching the proper floor. Alternatively, the elevator may be called when the bed begins its route such that the elevator is waiting for the patient causing no delay in movement. The elevator may then take the patient to the proper floor and the bed will begin communicating with that floor's WS for further movements.

Figure 5:
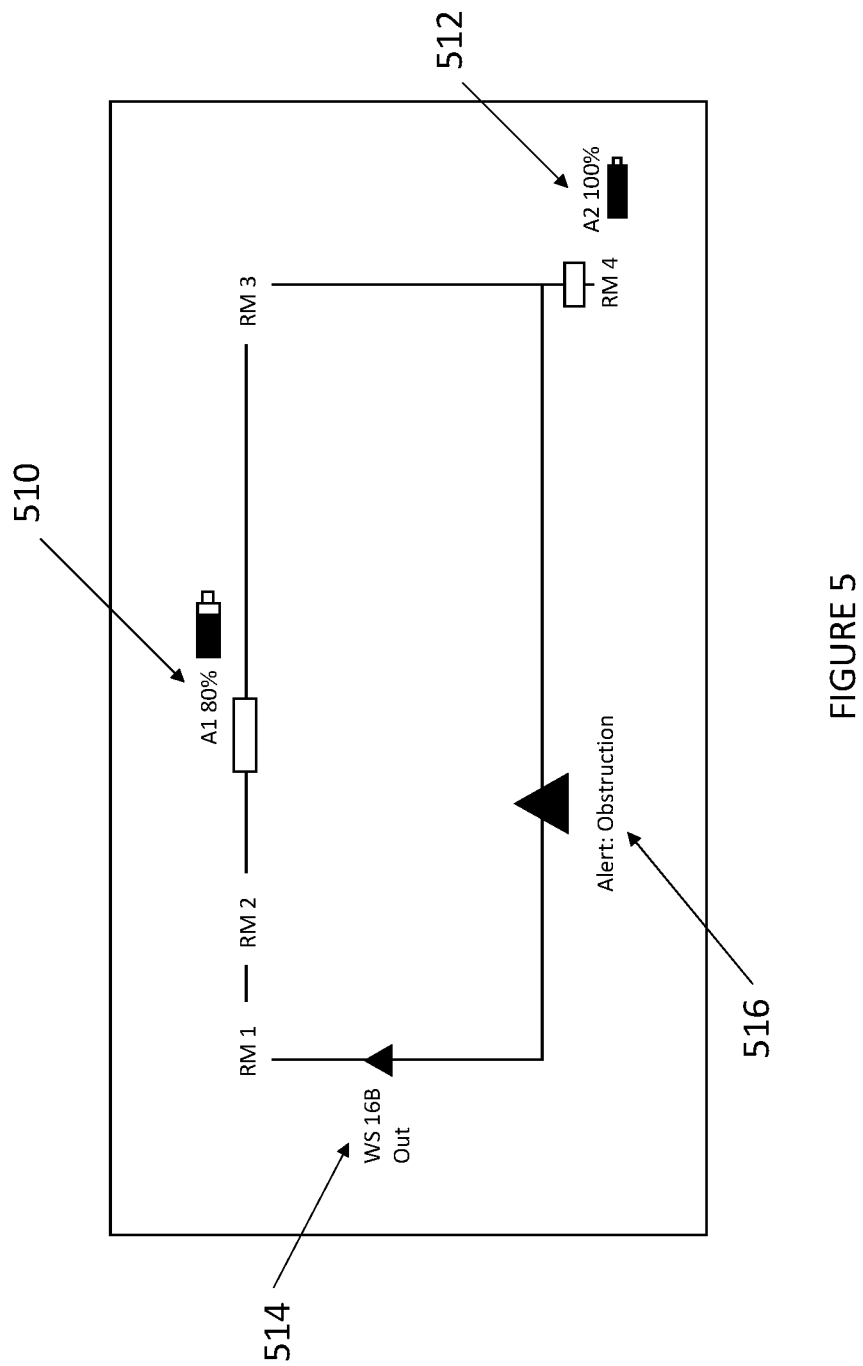
FIG. 5 is a visual representation of central management control.

The automated bed may be controlled by a remote operator of the central management system. The central management system may control and monitor all system activity. The location of automated beds as determined from the ABS and WS may be displayed to a central operator. An example display is depicted in FIG. 5. The display may include such indicators as bed location, bed identifiers, and battery percent 510, 512. The display may also include indicators for failed sensors 514. Detected obstructions 516 may also be depicted so appropriate action may be taken to remove the obstruction. Upon a new alert being sent to the central management system, the display may utilize sounds and blinking icons to draw immediate attention of the operator. The operator will be able to send commands to new beds or hospital personnel to correct any type of error. The operator will be able to override any preinstalled schedule instructions, or modify schedule instructions, to account for errors in the system.

Figure 6:
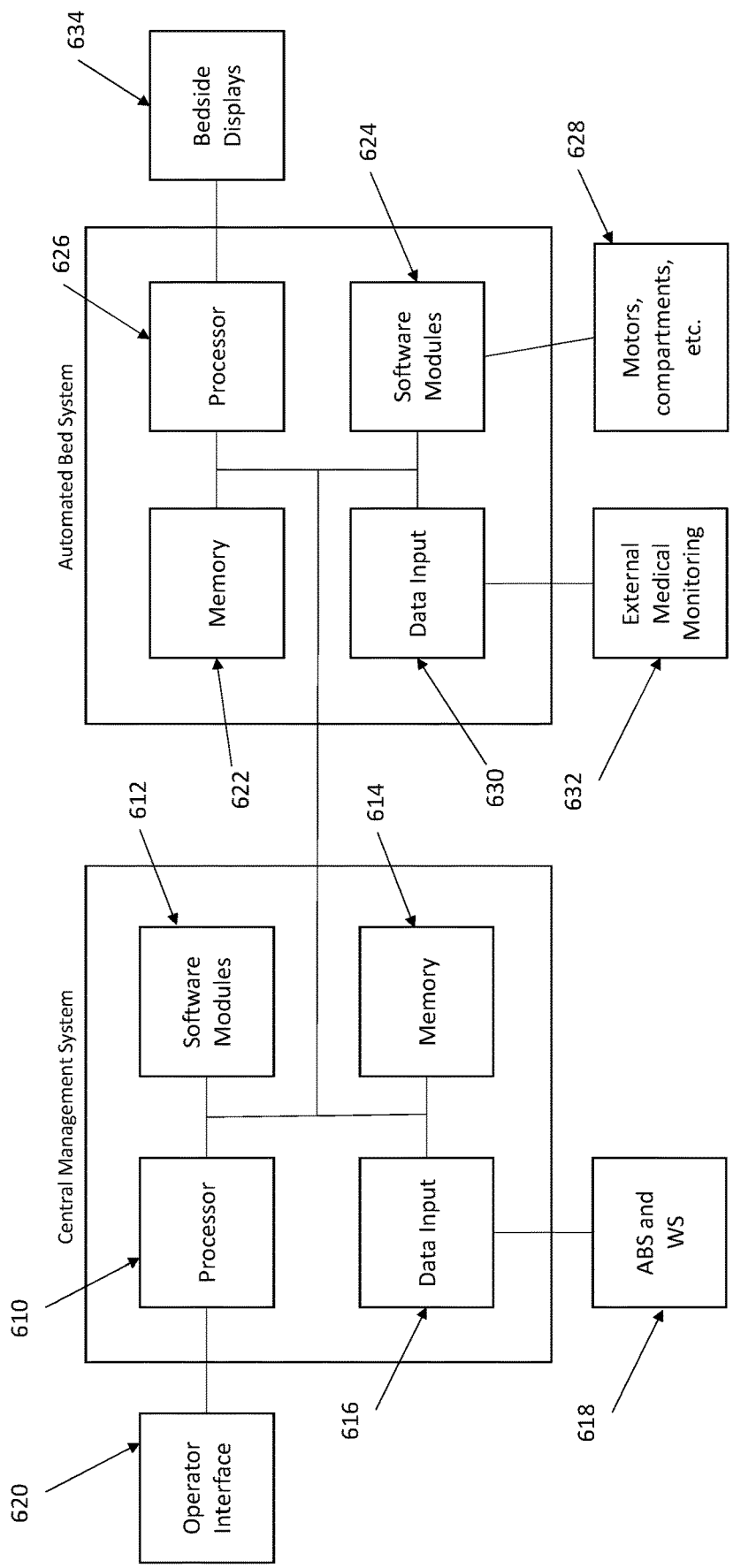
FIG. 6 is a visual depiction of electronic communication of the systems.

Referring to FIG. 6, a demonstrative electronic communication schematic is depicted between the central management system and the automated bed. The central management system may utilize a processor 610 to execute various software instructions 612 performing all functions of the system. The software instructions 612 may utilize information stored in a database 614. The database 614 may constantly be updated based on new incoming information 616. New data 616 may come from continuous signals received from ABS and WS 618 or operator input through a display interface 620. The operator interface 620 will allow for constant control and monitoring of the system.

The entire central management system will be able to communicate to a plurality of automated beds over wi-fi or any other communication means. The bed system may have its own database 622 to store certain software instructions 624 required for bed operations, such as patient history or schedules. The bed processor 626 may execute software instructions from both the bed 624 and central management systems 612 to control various bed functions, such as opening and closing of compartments or controlling motors 628. The bed system may constantly receive data 630 from a connected medical device 632, such as a heart rate monitor. Bedside displays 634 will act as a means for medical professional control of the bed system and monitoring of patient condition. Both the operational interface 620 and the bed displays 634 may require biometric authentication, or another authentication form, before reprogramming a bed schedule or function.

Should any bed lose power, the bed will still be capable of being manually pushed by any medical professional. In the event that one or more motors fails, the bed may automatically deploy the brakes to bring the unit to a stop, and await input from a medical profession to release the brakes, allowing for manual movement. Emergency switches will be included in every bed in case a medical professional senses something wrong with a bed. Possible switches may link to the immediate halt of the current function, such as moving, or link to an entire system shutdown, cutting all power to the bed. In case of emergency, a backup battery may be installed within the bed and tied to the essential functions of the bed, such as monitoring a patient's vitals.

Any embodiment of the present invention may include any of the optional or exemplary features of the other embodiments of the present invention. The exemplary embodiments herein disclosed are not intended to be exhaustive or to unnecessarily limit the scope of the invention. The exemplary embodiments were chosen and described in order to explain the principles of the present invention so that others skilled in the art may practice the invention. Having shown and described exemplary embodiments of the present invention, those skilled in the art will realize that many variations and modifications may be made to the described invention. Many of those variations and modifications will provide the same result and fall within the spirit of the claimed invention. It is the intention, therefore, to limit the invention only as indicated by the scope of the claims.

What is claimed is:

1. A system for patient management in a facility comprising:
   a plurality of beds each comprising:
      at least two wheels;
      at least one motor connected to said wheels;
      a controller in electronic communication with said motor; and
      a plurality of bed sensors;
   a plurality of wall sensors installed within the facility;
   a database;
   software instructions stored in said database;
   a processor;
   said processor adapted to execute the software instructions to send a signal to the controller causing the at least one motor to move the bed;
   said wall sensors adapted to detect the plurality of beds and transmit real-time bed location data to the processor;
   said bed sensors adapted to detect physical objects near the bed and transmit real-time obstruction data to the processor;
   said processor adapted to execute the software instructions to:
      analyze bed location data and obstruction data; and
      route the bed by sending a new signal to the controller; and
   wherein said bed automatically stops when an obstruction is detected by said bed sensors.

2. The system of claim 1 wherein:
   said processor is adapted to receive a user input requesting a bed movement; and
   said processor executes the software instruction to send a signal to the controller causing the at least one motor to move the bed in accordance with the received request.

3. The system of claim 1 further comprising:
   a unique identifier associated with each bed;
   a schedule stored within said database associated with at least one identified bed; and
   said processor adapted to execute the software instructions to send a signal to the controller of the associated bed causing the at least one motor to move the bed in accordance with the schedule.

4. The system of claim 1 further comprising:
   a unique identifier for each sensor; and
   said processor is adapted to receive an error identifying a malfunctioning sensor.

5. The system of claim 1 further comprising:
   a rechargeable battery installed within the plurality of beds;
   a plurality of charging pads installed within the facility;
   a retractable connection device installed on the bed; and
   said retractable connection device adapted to contact the charging pads.

6. The system of claim 5 wherein:
   said rechargeable battery provides power to at least one bed component;
   said database further comprises an essential or non-essential designation for each bed component; and
   said plurality of beds further comprises an emergency stop button adapted to disengage power for all non-essential bed components.

7. The system of claim 1 further comprising:
   at least one display monitor attached to each bed; and
   said processor adapted to display patient information on said at least one display monitor.

8. The system of claim 1 further comprising:
   a voice receiver installed in the plurality of beds;
   biometric information of facility personnel stored within said database; and
   said processor adapted to analyze voice commands and execute software instruction to implement the voice commands.

9. The system of claim 1 further comprising:
   a unique identifier associated with each bed;
   a schedule stored within said database associated with at least one identified bed;
   said schedule comprising at least one automated bed activity;
   said processor adapted to receive an override input from a user; and
   said processor adapted to halt all scheduled automated bed activities upon receiving said override input.

10. A system of patient management in a hospital facility comprising:
    a plurality of beds each comprising:
       at least two wheels;
       at least one motor connected to said wheels;
       at least one compartment with an electronic lock;
       a weight sensor;
       a rechargeable battery; and
       at least one display monitor;
    a plurality of charging pads installed within the facility;
    a database storing:
       software instructions;
       a unique identifier for each bed;
       patient information; and
       a unique identifier for each personnel;
    a processor;
    said processor adapted to execute the software instructions to:
       remotely control bed transportation; and
       automatically route an unused bed for charging based on the weight sensor and patient information.

11. The system of claim 10 further comprising:
a plurality of wall sensors installed within the facility;
a plurality of bed sensors installed on each bed;
said wall sensors adapted to detect the plurality of beds and transmit real-time bed location data to the processor;
said bed sensors adapted to detect physical objects near the bed and transmit real-time obstruction data to the processor;
said processor adapted to execute the software instructions to:
  analyze bed location data and obstruction data; and
  reroute the bed by sending a new signal to the controller.

12. The system of claim 11 wherein:
said plurality of wall sensors are installed such that all area of each facility hallway and each facility room is covered by at least two wall sensors.

13. The system of claim 10 further comprising:
an elevator installed within said facility;
said processor adapted to execute software instructions to at least cause:
  said elevator to ascend or descend to a designated floor;
  said elevator to open after arriving at said designated floor;
  said bed to enter the elevator; and
  said elevator to ascend or descend to a different floor after said bed has entered the elevator.

14. The system of claim 10 further comprising:
at least one medical monitoring device connected to said bed;
said at least one medical monitoring device adapted to transmit patient information to said processor; and
said processor adapted to execute software instructions to display said patient information on said at least one display monitor.

15. The system of claim 14 wherein:
said at least one display monitor further comprises a touch screen; and
said processor is adapted to receive a user input from said touch screen.

16. A method of transporting a bed with wheels in a hospital facility comprising:
installing a plurality of wall sensors in said facility;
installing a plurality of bed sensors on said bed;
assigning a unique identifier to each bed;
connecting at least one motor to the wheels, said motor adapted to receive a signal from a processor;
sending a signal from the processor to the motor to cause the identified bed to move based on wall sensor and bed sensor location;
storing a schedule for an identified bed within a database; and
sending a signal from the processor to the motor to cause the identified bed to move in accordance with the schedule.

17. The method of claim 16 further comprising:
transmitting from said bed sensors to said processor obstruction information; and
halting bed movement upon identifying an obstruction.

* * * * *